Figure 1:
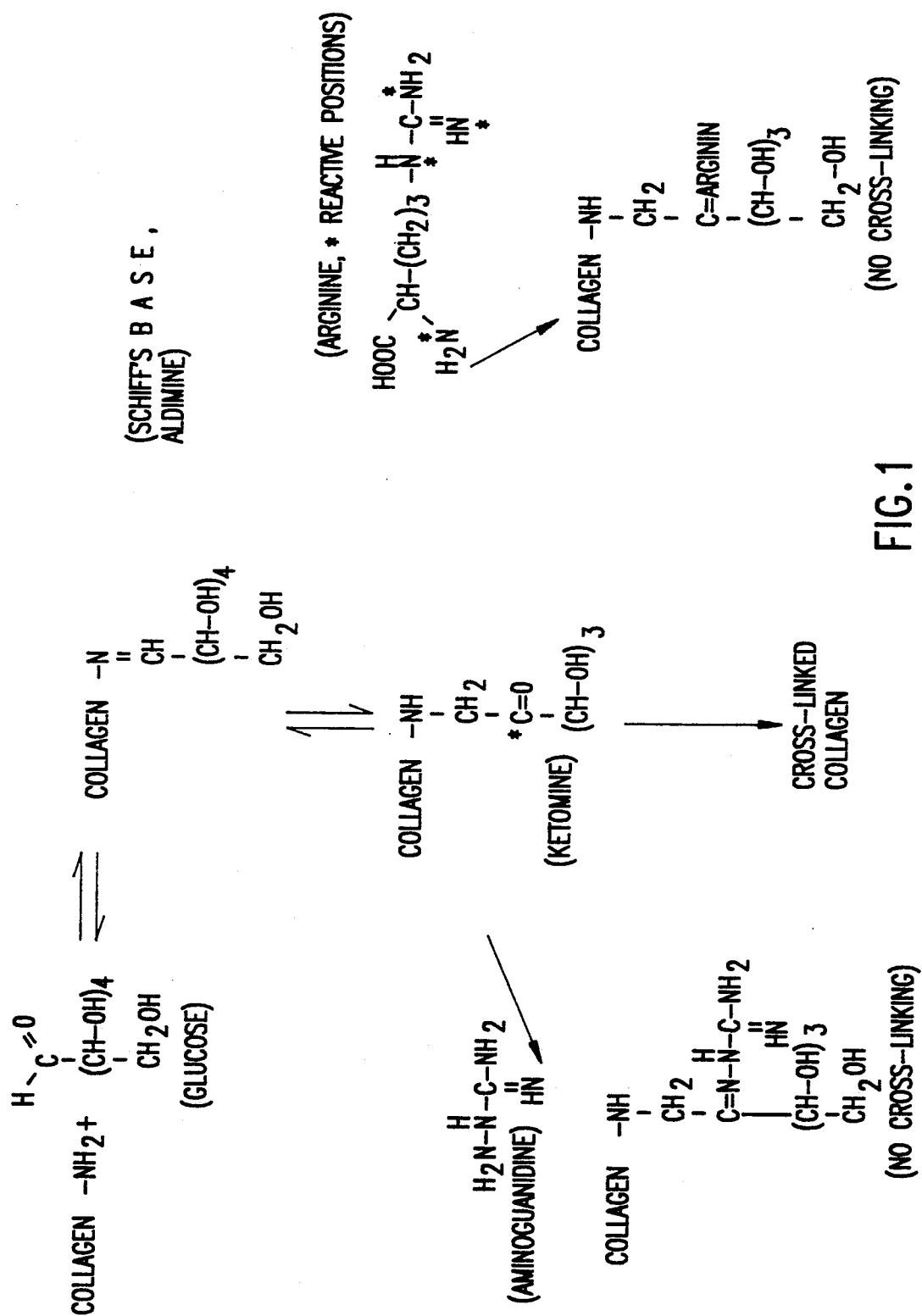

United States Patent [19]

Lubec

[11] Patent Number: 5,077,313
[45] Date of Patent: Dec. 31, 1991

[54] PROCESS FOR INHIBITING PATHOLOGICAL COLLAGEN CROSS-LINKING IN DIABETES PATIENTS

[76] Inventor: Gert Lubec, Brodschekhof 14, A-1220 Wien, Austria

[21] Appl. No.: 367,474

[22] Filed: Jun. 16, 1989

[30] Foreign Application Priority Data

Nov. 25, 1988 [AT] Austria .............................. A 2903/88
Mar. 6, 1989 [AT] Austria ............................... A 498/89
Apr. 20, 1989 [EP] European Pat. Off. ......... 89890116.0

[51] Int. Cl.$^5$ .................. A61K 31/195; A61K 31/155
[52] U.S. Cl. .................................... 514/565; 514/634; 514/866
[58] Field of Search ................ 514/561, 866, 565, 634

[56] References Cited

U.S. PATENT DOCUMENTS 4,308,257 12/1981 Caspe .................................. 424/180
4,758,583 7/1988 Cerami et al. ...................... 514/399

FOREIGN PATENT DOCUMENTS 0222313 5/1987 European Pat. Off. .
56-133213 10/1981 Japan .
2078516 6/1980 United Kingdom .

OTHER PUBLICATIONS

Extra Cellular Matrixes, p. 179, in Molecular Cell Biology Ed. by Darnell et al., 1986.
"Aminoguanidine Prevents Diabetes-Induced Arterial Wall Protein Cross-Linking", Science, vol. 232, No. 4758, Jun. 27, 1986, by M. Brownlee et al., pp. 1629-1632.
"Insulin and Glucagon Secretion in the Elederly", Chemical Abstracts, vol. 100, Mar. 26–Apr. 9, 1984, Abstract No. 97106h, by A. Pezzarossa et al.
The Merck Index, Tenth Edition, p. 113 (Arginine), p. 114, (Arginine Glutamate), p. 240 (Canavanine), p. 28 (Agmatine).
"Metabolism of L-[guanidinooxy-14C]Canavanine in the Rat", Chemical Abstracts, vol. 108, Feb. 1–Feb. 15, 1988, Abstract No. 48892t, by D. Thomas et al.

Primary Examiner—Thurman K. Page
Assistant Examiner—G. S. Kishore
Attorney, Agent, or Firm—Young & Thompson

[57] ABSTRACT

Pathological collagen cross-linking, caused in diabetes patients on account of the higher glucose concentrations, may be inhibited by means of arginine, spermidine, creatine, or agmatine, or a pharmaceutically acceptable salt thereof, in the amount of 1 to 4 g/day.

3 Claims, 3 Drawing Sheets

PROCESS FOR INHIBITING PATHOLOGICAL COLLAGEN CROSS-LINKING IN DIABETES PATIENTS

The present invention relates to the treatment of glucose-mediated collagen cross-links in diabetes-mellitus patients by means of arginine, spermidine, creatine or agmatine.

Diabetic conditions accelerate and alter the cross-linkage of long-lived proteins, such as collage (S. L. Schnider and R. R. Kohn, J. Clin. Invest. 66, 79 (1980), 67, 1630 (1981)). The above knowledge was the basis for intensive research, aiming at a non-enzymatic glycosylation of the above proteins. More recent studies suggest that advanced, non-enzymatic glycosylation products form the glucose-derived collagen cross-links (compare V. Monnier, A. Cerami, Science 211, 491 (1981) and M. J. C. Kent, N. D. Light, A. J. Bailey, Biochemical J. 225, 745 (1985)). The reaction diagram at the center of the accompanying FIG. 1 reflects a reaction mechanism for the above unusual cross-linkage.

Glucose reacts with the amino groups of proteins in a reversible, nucleophilic addition to form a Schiff's base adduct (aldimine), which then transforms into the more stable and still reactive Amadori product (compare H. B. Mortensen and C. Christophersen, Clin. Chim. Acta 134, 317 (1983)).

The resultant Amadori product then goes through a number of additional slower reactions with the amino groups of other proteins, forming glucose-derived, inter-molecular cross-links, such as 2(2-furoyl)-4(5)-(2-furanyl)-1H-imidazol, the recently described advanced glycosylation product (S. Pongor, P. C. Ulrich, F. A. Bencsath, A. Cerami, Proc. Natl. Acad. Sci. USA 81, 2684 (1984)).

Over longer periods of time, advanced glycosylation products accumulate continuously on long-lived proteins, such as collagen (M. Brownlee, H. Vlassara, A. Cerami in: Diabetes Complications, Scientific and Clinical Aspects, M. J. C. Grabbe, Ed. (Pitman, London 1986)).

The above age-dependent accumulation of advanced glycosylation products is accelerated in the collagen of diabetic persons on account of their long-term exposure to elevated glucose level (V. Monnier, R. R. Kohn, A. Cerami, Proc. Natl. Acad. Sci. USA 81, 583 (1984)). Based on the assumption that a glucose-mediated formation of protein cross-links could be prevented if the reactive carbonyls of the early glycosylation products (ketoamines) could be blocked pharmacologically, Brownlee and co-workers examined the influence of a nucleophilic hydrazine compound (aminoguanidine, $H_2N-C(=NH)-NH-NH_2$) on the course of the above reaction (M. Brownlee, H. Vlassara, A. Kooney, P. Ulrich, A. Cerami, Science 232, 1629 (1989)). They demonstrated that aminoguanidine prevents the in-vitro formation of advanced glycosylation products and the glucose-induced collagen cross-links (see FIG. 1, lower left). Their results also demonstrated that aminoguanidine, administered to rats, inhibits the diabetes-induced accumulation of advanced glycosylation products and an abnormal protein cross-linking in the connective tissue of arterial walls. The effect of aminoguanidine on the formation of advanced glycosylation products was evaluated by measuring specific fluorescence, as was described before for collagen.

Concerning albumin glycosylation, it was observed that aminoguanidine prevents the formation of an advanced albumin glycosylation product, whereas the Amadori reaction takes place more or less unchanged.

The effect of aminoguanidine on in-vitro collagen cross-linking was determined by means of sodium dodecyl sulfate polyacryamide gel electrophoresis (SDS-PAGE) of cyanogen bromide cleavage products of native collagen fibrils. In the course of time, the gel pattern of the cyanogen bromide cleavage products derived from collagen, which was incubated with glucose, showed higher values for cross-linked peptides with a high molecular weight. The presence of aminoguanidine in the incubation mixture reduced significantly the amount of cross-linked peptides with a high molecular weight.

The in-vivo effect of aminoguanidine was demonstrated on non-diabetic and alloxan-diabetic rats. Intraperitoneal injections of aminoguanidine were administered daily. The amounts of the resultant fluorescent advanced non-enzymatic glycosylation products were determined. The extent of cross-linking of the connective tissue of the aorta was lower in the animals treated with aminoguanidine than in the untreated animals.

Collagen solubility, a further parameter for cross-linking, decreased to normal values in the animals treated with aminoguanidine.

Like most hydrazines, aminoguanidine also has an extremely high toxicity. It can therefore not be used for practical purposes.

It is the object of the present invention to provide substances which inhibit the formation of cross-links in collagen proteins by a mechanism similar to that of aminoguanidine and which are non-toxic.

The present invention comprises the use of arginine, particularly of L(+)-arginine ($HCOOC-CH(NH_2)-(CH_2)_3-NH-C(NH)-NH_2$) of agmatine, which is the decarboxylation product of arginine ($CH_2(NH_2)-(CH_2)_3-NH-C(NH)-NH_2$), of spermidine (N-(3-aminopropyl)-1.4-butanediamine, $H_2N-(CH_2)_3-NH-(CH_2)_4-NH_2$) or of creatine (N-amidinosarcosine, $H_2N-C(NH)-C(CH_3)-CH_2-COOH$), at certain high dosage levels significantly above those at which these substances are found endogenously or normally ingested exogenously.

Arginine is a non-toxic amino acid, which is contained in all proteins of the daily diet. Spermidine and creatine are found in the human body in significant amounts. But none of these is thus present in the human body at levels found to be effective according to the present invention.

The free base of L-arginine was used for the below investigations.

The following in-vitro studies were carried out:
1. Fluorescence test according to the method by V. Monnier et alii (see above).
2. SDS-PAGE of glucose-incubated, isolated collagens, with and without L-arginine, using aminoguanidine as control substance.
3. Incubation tests with various collagen preparations, interstitial collagens and basal-lamina collagen.

The following in-vivo experiments were carried out, using both Swiss mice and KK mice with spontaneous diabetes:
4. Solubility tests.
5. SDS-PAGE of isolated collagens.

6. Kidney-weight determination by means of autopsy (serum parameter: fructosamine).
7. Non-enzymatic glycosylation test series and
8. Fluorescence test series.

As mentioned before, two different types of test animals were used for the in-vivo tests, i.e. Swiss mice and KK mice with spontaneous diabetes.

The administered daily oral dosage was 50 mg/kg body weight, for a period of 5 weeks.

Neither clinically, nor at autopsy, were any side-effects observed.

This tallies with clinical reports by scientists, who had examined arginine for other purposes, e.g. as diet supplement for healthy persons and for certain diseases, such as arginosuccinicaciduria, asthenospermia and immunomodulation.

In addition, arginine is commercially available, e.g. in pharmacies, without prescription, and the FDA in the USA has approved it as a diet supplement.

IN-VITRO EXPERIMENTS

1. Fluorescence test series for collagen type I (interstitial collagen), with non-enzymatic glycosylation in vitro, and type III.

In its native state, collagen was incubated with 200 mM glucose, both in the presence and in the absence of arginine, or aminoguanidine respectively, at equi-molar conditions by means of the method according to Brownlee (M. Brownlee, H. Vlassara, A. Kooney, P. Ulrich, A. Cerami, Science 232, 1629 (1986)). Collagens without glucose in the incubation medium were used as control samples. For aminoguanidine and arginine, a significant fluorescence inhibition was observed for all collagen types when using the method according to, Monnier and co-workers (V. Monnier, R. R. Kohn, A. Cerami, Proc. Natl. Acad. Sci. USA 81, 583 (1984)).

2. An SDS-PAGE according to the method by Brownlee, with the modification that the collagen cleavage products were obtained by means of collagenase digestion rather than cyanogen bromide cleavage, yielded collagen cleavage products of higher molecular weights than in the samples without aminoguanidine, or arginine respectively. A molecular-weight pattern was observed for the samples containing arginine, or aminoguanidine respectively, which resembled that of the non-glycosylated collagen.

3. An analogous test, using basal-lamina collagen, type IV, revealed the arginine activity in relation to this vascular collagen system.

IN-VIVO EXPERIMENTS

Normal Swiss rats, 10 animals per group, white, female, age - 1 year, were treated for 6 weeks with arginine, with the daily oral dosage consisting of 50 mg arginine/kg body weight, diluted in tap water. The test animals had free access to solid feed, i.e. rat chow. Ten corresponding animals were used as controls.

4. Solubility test:
Collagen was extracted from the skin, liver and kidney of the test animals. There was no difference in collagen extractability between the groups of treated and untreated test animals.

5. SDS-PAGE revealed no differences between the extracted collagens of the two groups of test animals, which proves that there is no effect on normal cross-linking.

6. At autopsy, no differences were observed between the two groups of test animals. There were neither differences in the weight of the organs, nor any pathological findings.

7. There was a significant difference in the non-enzymatic glycosylation of the serum protein, which could be expressed by means of a fructosamine test. The group with arginine treatment showed lower amounts of non-enzymatic glycosylations of the serum protein. This has an impact on the non-enzymatic glycosylation, which also takes place under physiological conditions to some extent.

8. Fluorescence according to the above-mentioned methods in the collagen extracted from the skin, liver and kidney showed significant differences, which demonstrated the positive impact of the non-enzymatic glycosylation, i.e. a decrease of the above process.

Ten month-old KK mice, white, female, obese and diabetic, were treated with arginine for a period of 5 weeks. The same dosage was used, as indicated above. Ten KK mice served as controls. The protocol was drafted as for the Swiss mice.

9 Solubility test:
Collagen was extracted from the skin, liver and kidney of the test animals. There was a significant difference, since the solubility was considerably higher in the treated animals than in the untreated control animals, which reveals a positive pharmacological effect of the arginine, since low solubility in the diabetic state is one of the pathogenic factors for long-term complications of this disease.

10. SDS-PAGE revealed significant divergences. Untreated KK mice produced collagen cleavage products with a higher molecular weight than the treated KK mice. This demonstrated the positive effect of arginine upon cross-linking and non-enzymatic glycosylation.

11. At autopsy, no differences could be noticed in the gross appearance. No macroscopic pathological findings were obtained for either of the two groups; yet, the autopsy of the diabetic mice (in analogy to human patients) showed that the untreated mice have a significantly higher kidney weight than the mice treated with arginine.

12. The serum fructosamine concentrations, expressed as morpholine fructose, were lower in the animals treated with arginine, which was of statistical relevance. This demonstrates a positive pharmacological effect upon non-enzymatic glycosylation.

13. Fluorescence tests with the collagens isolated from the mice showed significantly lower values for the treated mice, which indicates the positive effect upon non-enzymatic glycosylation.

The data, described above, showed the positive in-vitro and in-vivo effect of arginine, which is similar to the agminoguanidine activity, i.e. inhibition of the fatal glucose-induced cross-linking of collagen in diabetic conditions.

The reaction mechanism with arginine for collagen protein in its glycosylated form is shown at the right of FIG. 1. At any one of its reactive locations, marked by an asterisk, arginine can react with the active carbonyl group of the ketoamine. The reaction with spermidine, creatine or agmatine corresponds to the reaction mechanism shown for arginine in the reaction diagram.

Instead of arginine, creatine, spermidine or agmatine, a pharmaceutically acceptable salt thereof (e.g. glutamate) or an analogous product thereof (e.g. canavanine, as an analogous product of arginine) can be used. Such analogous products, although not specifically recited in the appended claims, are nevertheless hereby defined as equivalents of those specifically recited compounds and so are within the scope of the appended claims.

The KK-mice tests were carried out on db/db mice with spontaneous diabetes from the United Kingdom. The same correlating results could be obtained for this system as for the KK mice. This system too, is a suitable model for type-II diabetes.

The kidney tissue, taken from KK mice with diabetus-mellitus from the FRG, was studied by means of electron microscopy. Vascular (glomerulum) basal-lamina thickness was evaluated by means of morphometry, mesangium proliferation was measured, and the animals treated with L-arginine were compared to the untreated controls.

The panel of treated animals had significantly lower basal-lamina values and a significantly reduced mesangium proliferation.

Figure 2:
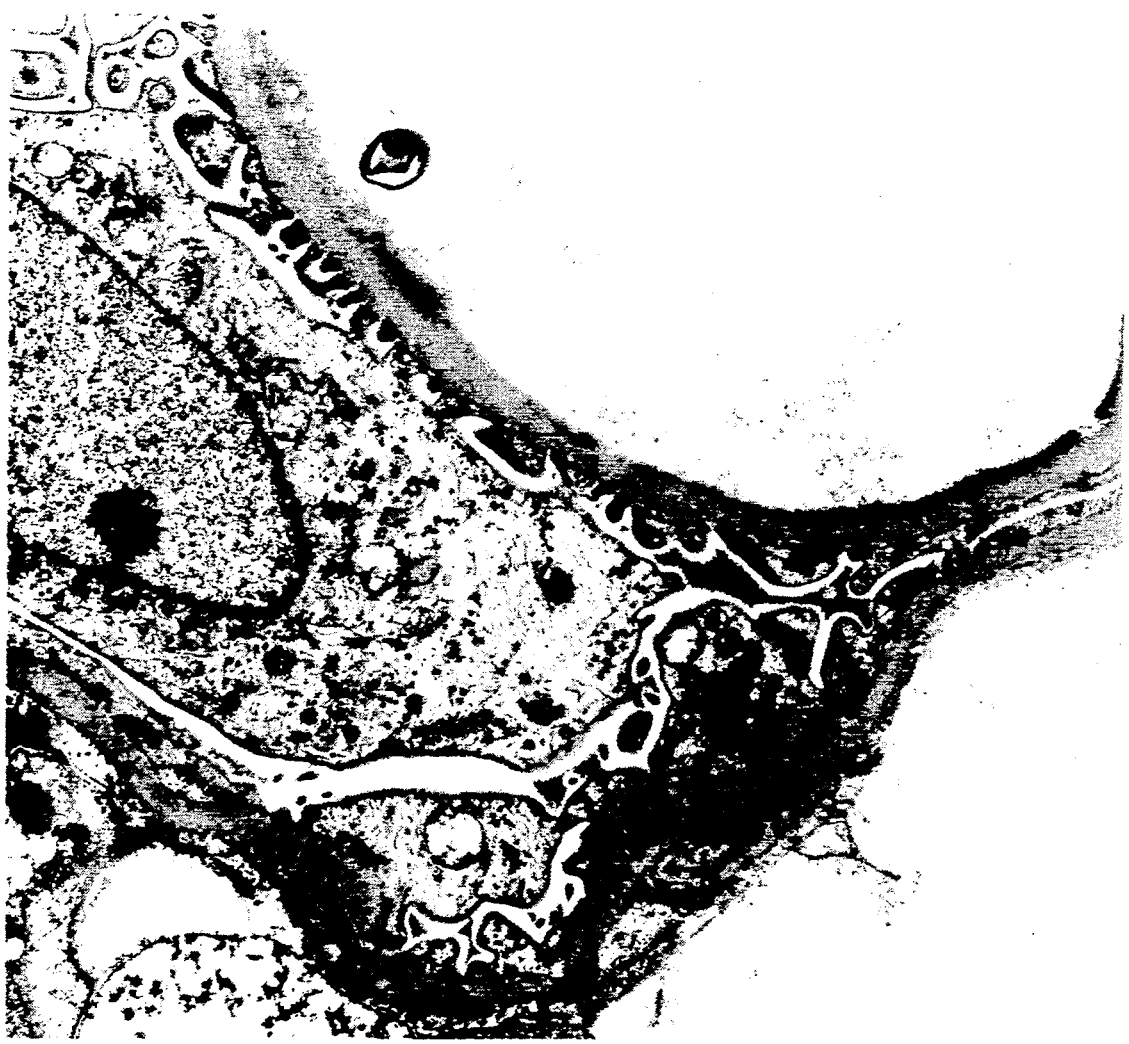
Figure 3:
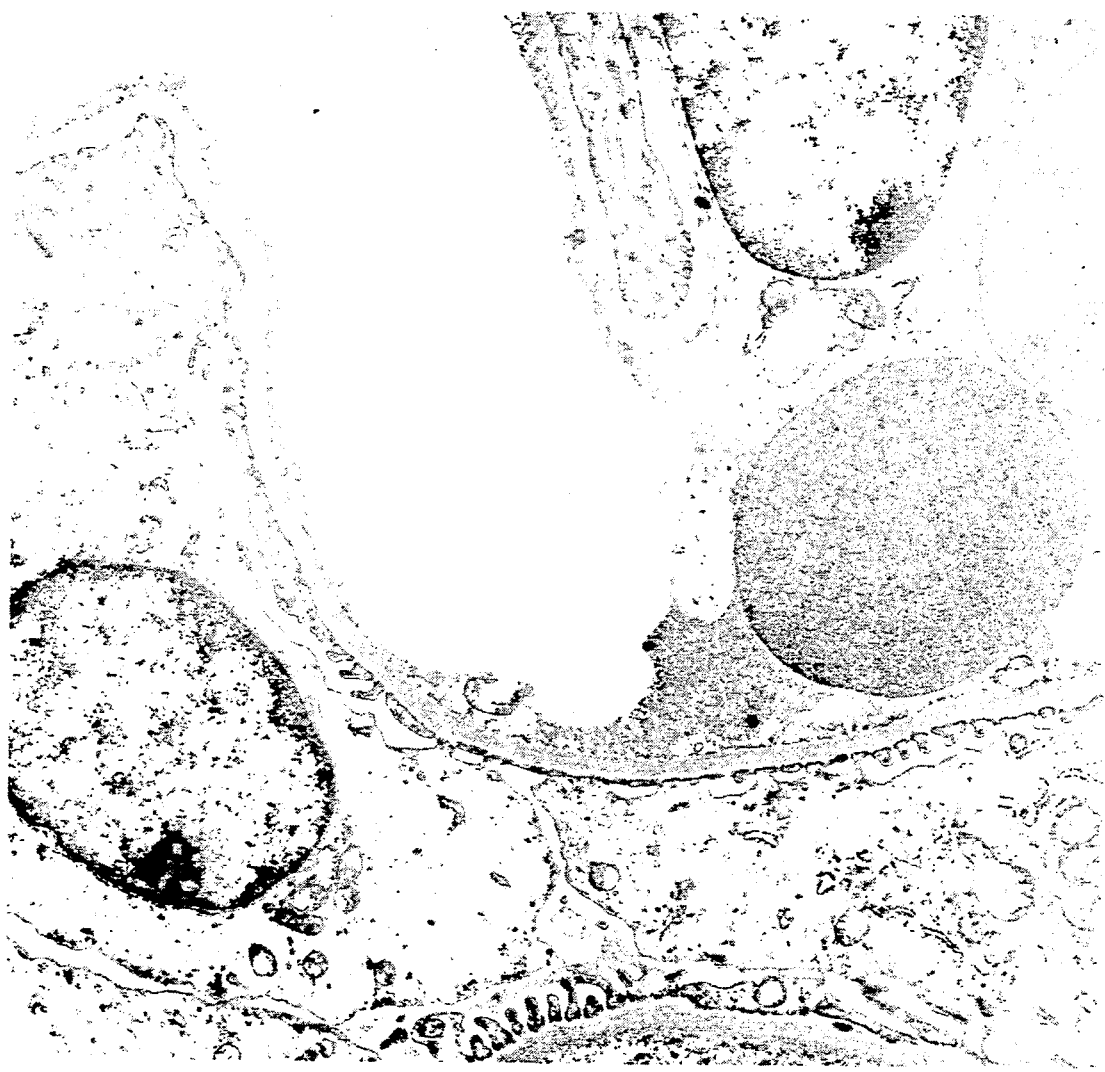
Figure 1:

In the accompanying drawings:

FIG. 1, as indicated above, is a display of the various reaction diagrams described;

FIG. 2 is an electron-microscopic presentation of a glomerulum without arginine treatment, taken from a KK mouse; and FIG. 3 shows a glomerulum with the same enlargement factor, taken from a KK mouse treated with arginine.

A comparison shows that the basal lamina of FIG. 2 is thicker than in FIG. 3 and that the mesangium proliferation is lower in FIG. 2. FIG. 3 does not show any mesangium proliferation and a thinner glomerulum basal lamina.

The tests made with the free L-arginine base were also carried out with agmatine. The results obtained were comparable to the results obtained with the tests described above.

Tests made on animals with streptomycine-induced diabetes showed comparable results.

Tests on spontaneous diabetic BB rats showed also corresponding results.

The tests made using arginine or agmatine were also performed with spermidine and creatine. The tests showed results that were comparable to the results obtained with the above tests.

The types of animals used for the tests reflect the possibilities of treatment, in case of type-I and type-II diabetes.

Suitable pharmaceutical preparations, inhibiting collagen cross-linkage, are manufactured advantageously and in a simple manner by combining arginine, spermidine, creatine, agmatine, a salt or analogous product thereof, with pharmaceutically suitable, chemically inert fillers, carriers, stretching agents or excipients, as they are generally used for the manufacture of medical preparations for oral or parenteral application, or for local injection, and as are generally and collectively referred to as "excipients" in the present specification and claims. The compounds according to the present invention may be compounded or formulated in the form of tablets, powders, capsules, suspensions, solutions, emulsions and similar dosage forms. The preparations may be manufactured by mixing arginine, spermidine, creatine, agmatine, an analogous product or salt thereof, preferably in water-soluble form, with the above conventional diluents or tabletting additives, such as cellulose powder, corn starch, lactose, talcum, stearic acid, magnesium stearate, rubber or the like, in keeping with known and conventional manufacturing methods that have become established in the industry.

If the product is intended for parenteral application or local injection, the substances according to the present invention may preferably be combined in their non-toxic, water-soluble form with carriers such as water, salt solution, glucose solution or alike.

Effective amounts of any of the compounds according to the present invention may be administered to the body of a diabetes patient according to one of several methods, e.g. orally, i.e. by means of capsules or tablets, parenterally in the form of sterile solutions or suspensions, intravenously in sterile solutions, or locally in the form of sterile solutions or suspensions.

The daily dosage level for an adult human is 1 to 4 g/day, preferably about 3 g/day. Below about 1 g/day, the compounds of the present invention are not effective. Above about 4 g/day, the compounds are in substantial excess of the required amount and so are medically unjustifiable.

A typical dosage form is a tablet consisting of 0.5 g arginine in 4 g crushed linseed as an excipient, or a gelatine capsule containing 0.5 arginine, a typical dosage regimen being the oral administration of two such capsules or tablets three times a day.

What is claimed is:

1. A process for inhibiting glucose-mediated collagen cross-linking in diabetes patients, comprising administering to a diabetes patient in the need of same an amount from about 1 to about 4 g per day of a compound selected from the group consisting of arginine, creatine, agmatine and pharmaceutically acceptable salts thereof, thereby to inhibit glucose-mediated collagen cross-linking in diabetes patients.

2. A process as claimed in claim 1, in which said amount is about 3 per day.

3. A process as claimed in claim 1, in which said compound is administered orally.

* * * * *

UNITED STATES PATENT AND TRADEMARK OFFICE
CERTIFICATE OF CORRECTION

PATENT NO. : 5,077,313

DATED : 12/31/91

INVENTOR(S) : Gert Lubec

It is certified that error appears in the above-identified patent and that said Letters Patent is hereby corrected as shown below:

The title page, should be deleted to be replaced with the attached title page.

The drawing sheet consisting of Fig. 1, should be deleted and replaced with the attached drawing sheet consisting of Fig. 1.

Signed and Sealed this

Twenty-second Day of June, 1993

Attest:

MICHAEL K. KIRK

*Attesting Officer*     *Acting Commissioner of Patents and Trademarks*

United States Patent
Lubec

[11] Patent Number: 5,077,313
[45] Date of Patent: Dec. 31, 1991

[54] PROCESS FOR INHIBITING PATHOLOGICAL COLLAGEN CROSS-LINKING IN DIABETES PATIENTS

[76] Inventor: Gert Lubec, Brodschekhof 14, A-1220 Wien, Austria

[21] Appl. No.: 367,474

[22] Filed: Jun. 16, 1989

[30] Foreign Application Priority Data

Nov. 25, 1988 [AT] Austria .......................... A 2903/88
Mar. 6, 1989 [AT] Austria .......................... A 498/89
Apr. 20, 1989 [EP] European Pat. Off. ........ 89890116.0

[51] Int. Cl.$^5$ .................. A61K 31/195; A61K 31/155
[52] U.S. Cl. ............................... 514/565; 514/634; 514/866
[58] Field of Search ................ 514/561, 866, 565, 634

[56] References Cited

U.S. PATENT DOCUMENTS 4,308,257 12/1981 Caspe ................................ 424/180
4,758,583 7/1988 Cerami et al. ..................... 514/399

FOREIGN PATENT DOCUMENTS 0222313 5/1987 European Pat. Off.
56-133213 10/1981 Japan
2078516 6/1980 United Kingdom

OTHER PUBLICATIONS

Extra Cellular Matrixes, p. 179, in Molecular Cell Biology Ed. by Darnell et al., 1986.
"Aminoguanidine Prevents Diabetes-Induced Arterial Wall Protein Cross-Linking", Science, vol. 232, No. 4758, Jun. 27, 1986, by M. Brownlee et al., pp. 1629-1632.
"Insulin and Glucagon Secretion in the Elederly", Chemical Abstracts, vol. 100, Mar. 26-Apr. 9, 1984, Abstract No. 97106h, by A. Pezzarossa et al.
The Merck Index, Tenth Edition, p. 113 (Arginine), p. 114, (Arginine Glutamate), p. 240 (Canavanine), p. 28 (Agmatine).
"Metabolism of L-[guanidinooxy-14C]Canavanine in the Rat", Chemical Abstracts, vol. 108, Feb. 1-Feb. 15, 1988, Abstract No. 48892t, by D. Thomas et al.

Primary Examiner—Thurman K. Page
Assistant Examiner—G. S. Kishore
Attorney, Agent, or Firm—Young & Thompson

[57] ABSTRACT

Pathological collagen cross-linking, caused in diabetes patients on account of the higher glucose concentrations, may be inhibited by means of arginine, spermidine, creatine, or agmatine, or a pharmaceutically acceptable salt thereof, in the amount of 1 to 4 g/day.

3 Claims, 3 Drawing Sheets

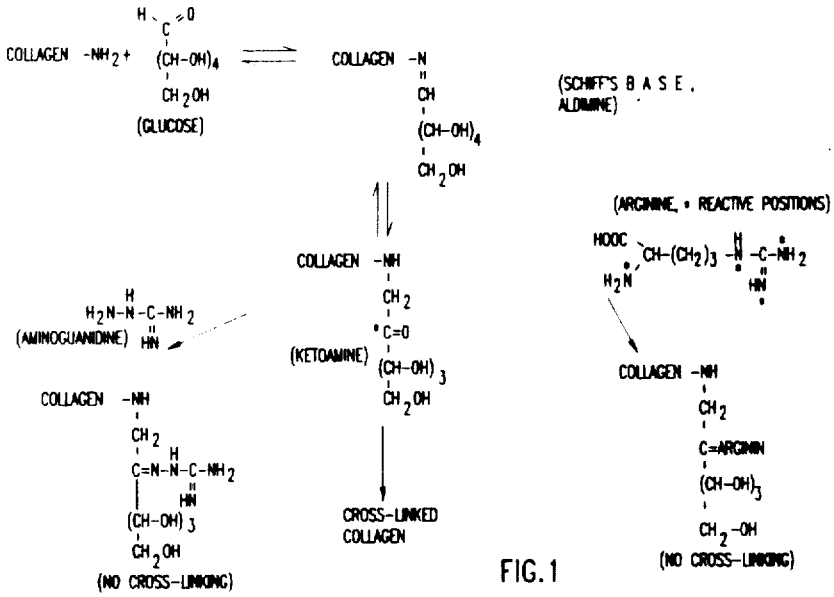

FIG. 1